United States Patent [19]

DiMatteo

[11] 4,225,228

[45] Sep. 30, 1980

[54] SURFACE COATING FOR OPTICAL INSPECTION

[75] Inventor: Paul L. DiMatteo, Huntington, N.Y.

[73] Assignee: Solid Photography Inc., Melville, N.Y.

[21] Appl. No.: 4,300

[22] Filed: Jan. 18, 1979

[51] Int. Cl.³ .............................................. G01N 1/00
[52] U.S. Cl. ...................................... 356/36; 209/3.1; 356/445
[58] Field of Search ................ 356/36, 445, 446, 447, 356/448; 209/3.1, 3.3

[56] References Cited

U.S. PATENT DOCUMENTS 3,734,628   5/1973   Michishita et al. ................ 356/36 X Primary Examiner—Vincent P. McGraw
Attorney, Agent, or Firm—Max Fogiel

[57] ABSTRACT

An arrangement for coating a surface preparatory to optical inspection. The surface to be inspected for geometrical, physical or chemical characteristics, is cooled to a temperature below freezing. The surface is then sprayed with water and a layer of frost is allowed to form on the surface. The cooling procedure may be achieved by refrigeration coils or by cold air applied to surfaces of objects to be inspected, as the objects proceed along a conveyor belt on a path to an optical inspection station. The water spray may be in the form of low pressure water vapor whereby a thin layer of frost or water droplets coat the objects. The objects are kept cool during the inspection process, and they are not allowed to warm up to room temperature until the inspection process is completed. The frost or water droplets disappear after the objects are permitted to warm up, so that the coating applied prior to the optical inspection, is removed in an efficient manner at negligible cost. The frost or water droplets provide support to optical inspection methods which are best satisfied by lambertian reflectance characteristics.

12 Claims, 1 Drawing Figure

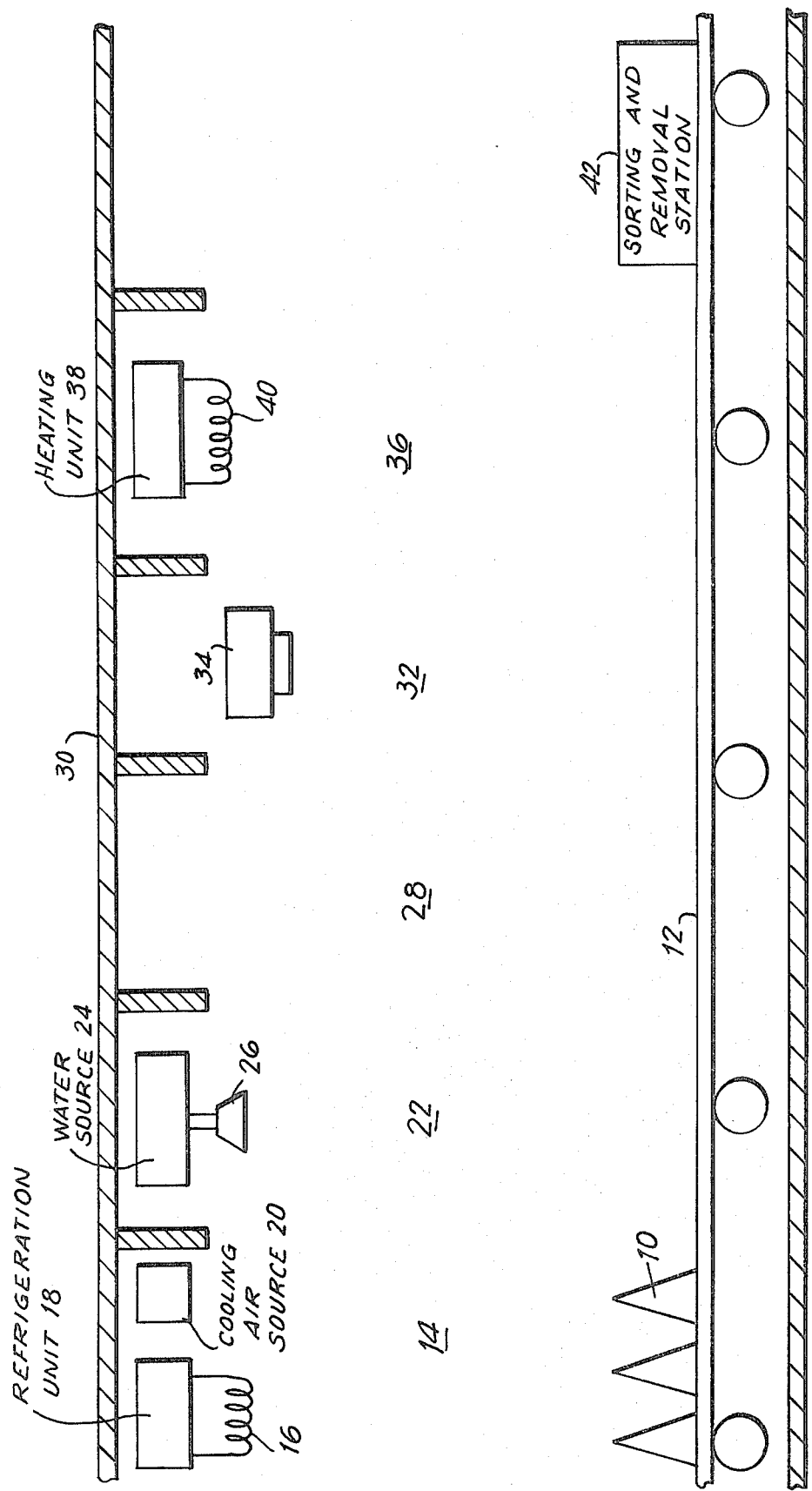

SURFACE COATING FOR OPTICAL INSPECTION

BACKGROUND OF THE INVENTION

In the manufacture of parts or articles such as bottles, for example, it is often desirable to optically inspect the surfaces of such articles or objects. However, the surfaces of such objects are often not suitable for optical viewing. Surfaces that are transparent, translucent, black or specular, are particularly difficult to view optically. The ideal surface for viewing is one which is white and lambertian, such as a surface which has been painted flat white. However, painting an object white before inspection is tedious and the paint removal following the inspection is expensive.

Accordingly, it is an object of the present invention to prepare the surface of an object for optical inspection without requiring that the surface be painted.

Another object of the present invention is to provide an arrangement of the foregoing character which may be carried out in a simple manner and which may be applied economically.

Another object of the present invention is to provide an arrangement of the foregoing character in which the surface coating applied preparatory to optical inspection may be quickly removed without applying special techniques.

Further object of the present invention is to provide an arrangement, as described, in which the characteristics of the surface remain unaffected by the coating applied for optical inspection.

SUMMARY OF THE INVENTION

An arrangement for preparing a surface prior to optical inspection. The surface of an object to be inspected, is cooled by refrigeration coils or by cold air, as the object travels along a conveyor belt on the way to an optical inspection station. After the cooling procedure, the object is sprayed with low pressure water vapor so that a thin layer of frost or water droplets are formed on the object surface.

During the inspection procedure, the object surface is kept cool by the application of cold air or refrigeration coils.

After the inspection procedure has been completed, the object is allowed to warm up to room temperature. Upon the completion of such a warm-up period, the coating of frost or water droplets disappears, leaving the object surface in its initial state.

To obtain a coating of frost, the object temperature is dropped below freezing at the time water vapor is introduced. The object surface is also kept below freezing during the inspection procedure.

To obtain a coating of water droplets in liquid form, the temperature of the object surface is maintained above freezing and below the dew point.

Whether the surface coating is in the form of frost or water droplets in liquid form, the object surface characteristic becomes modified so as to enhance optical inspection methods which rely on lambertian reflectance characteristics.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

A schematic view showing the arrangement for applying a surface coating to an object in preparation to optical inspection, in accordance with the present invention.

DESCRIPTION OF THE PREFERRED EMBODIMENTS

Articles tend to be inspected on their surface, are transported or conveyed on a conveyor belt 12 to a cooling station 14. This station can be equipped with cooling coils 16 connected to a refrigeration unit 18. A source of cooling air 20 may also be provided.

If a coating or frost is to be applied to the surface of the articles or objects 10, then the articles are cooled to a temperature below freezing. If, on the other hand, the surfaces of the articles are to be covered with water droplets in liquid form, then the temperature of the articles is held above freezing but below the dew point.

After passing through the cooling station 14, the articles are sprayed with low pressure water vapor within the spraying station 22. The water vapor is derived from a source 24 and applied by a spray head 26.

After the spraying procedure has been completed, the articles pass through the zone 28 where the frost coating or water droplets are allowed to be formed on the surface of the articles or objects 10. The zone 28 within the housing 30 enclosing the processing stations, has a length along the conveying direction, which allows sufficient time for the frost or water droplets coating to be formed.

Upon arriving at the inspection station 32 from the coating forming zone 28, the surfaces of the articles 10 are prepared suitable for optical inspection. At the inspection station 32, the temperature of the articles is maintained below freezing during the inspection process, if the coating of frost is to be retained. If, on the other hand, the articles are to be covered with water droplets in liquid form, the temperature of the articles during inspection, is kept above freezing but below the dew point. In either case, the surfaces of the articles 10 have their characteristics modified so as to enhance the optical inspection methods which may be applied and which are best satisfied by lambertian reflectance characteristics. Inspection means 34 may be in the form of a camera, for example, microscopic equipment, and other optical inspection instruments, for example. Such instruments may be used to measure surface roughness, dimensions of the articles, surface curvature, and the like.

When the inspection procedure has been completed while the articles pass through the zone 32, the articles arrive at zone 36 where the coating on the articles is removed. For purposes of removing the coating of either frost or water droplets, the articles may be simply allowed to warm up as they travel through the zone 36. In this manner, the coating is removed in a very economical manner, since no special techniques need be applied. If, on the other hand, it is desired that the coating be removed more rapidly than is possible by taking no other steps than to allow the articles to be warmed up to room temperature, heat may be applied from a unit 38 in the zone 36 through heating coils 40. With such an arrangement of the heating unit 38 and coils 40, the warm-up process may be carried out more rapidly and the length of zone 36 may, for example, be shortened from the length necessay if the articles are to be allowed to warm up to room temperature without the influence of other means.

After passage through the zone 36, the articles may be sorted and removed in accordance with the findings at the inspection station, within the sorting and removal unit 42, for example.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention, and therefore, such adaptations should and are intended to be comprehended within the meaning and range of equivalence of the following claims.

What is claimed is:

1. A method for optical inspection of a surface, comprising the steps of: cooling the surface below a predetermined temperature; spraying the surface with water; forming a refrigerated layer of water on said surface to provide a surface of predetermined characteristics for optical inspection; inspecting said surface optically while said refrigerated layer is present; and raising the temperature of said surface to remove said refrigerated layer.

2. A method as defined in claim 1, wherein said surface is cooled below freezing temperature to form a layer of frost.

3. A method as defined in claim 1, wherein said surface is cooled to a temperature above freezing and below dew point to form water droplets in liquid form.

4. A method as defined in claim 1, wherein said surface is sprayed with water vapor after cooling below said predetermined temperature.

5. A method as defined in claim 4, wherein said water vapor comprises low pressure water vapor.

6. A method as defined in claim 1, wherein said refrigerated layer has a substantially white appearance.

7. Apparatus for carrying out the method for optical inspection of a surface as defined in claim 1, comprising: means for cooling the surface below a predetermined temperature; means for spraying the surface with water; means for forming a refrigerated layer of water on said surface to provide a surface of predetermined characteristics for optical inspection; means for inspecting said surface optically while said refrigerated layer is present; and means for raising the temperature of said surface to remove said refrigerated layer.

8. Apparatus as defined in claim 7 wherein said surface is cooled below freezing to form a layer of frost.

9. Apparatus as defined in claim 7 wherein said surface is cooled to a temperature above freezing and below dew point to form water droplets in liquid form.

10. Apparatus as defined in claim 7 wherein said surface is sprayed with water vapor after having been cooled.

11. Apparatus as defined in claim 10 wherein said water vapor comprises low pressure water vapor.

12. Apparatus as defined in claim 7 wherein said refrigerated layer has substantially lambertian reflectance characteristics.

* * * * *